United States Patent [19]
Eldridge, Jr.

[11] 3,944,069
[45] Mar. 16, 1976

[54] RECEIVER FOR DISPOSABLE SURGICAL IMPLEMENTS

[75] Inventor: John D. Eldridge, Jr., Anaheim, Calif.

[73] Assignee: Instranetics, Inc., Fullerton, Calif.

[22] Filed: Jan. 8, 1974

[21] Appl. No.: 431,629

Related U.S. Application Data

[63] Continuation-in-part of Ser. No. 868,317, Oct. 22, 1969, abandoned, and a continuation-in-part of Ser. No. 182,588, Sept. 22, 1971, abandoned.

[52] U.S. Cl. .............. 206/350; 206/63.3; 206/365; 206/382; 206/460; 206/813
[51] Int. Cl. ... A61l 17/02; B65d 73/00; B65d 85/24
[58] Field of Search............ 128/1.3; 150/34, 52 R; 206/63.3, 234, 339, 350, 363, 365, 366, 370, 380, 382, 460, 812, 813, 818; 211/DIG. 1; 335/303

[56] References Cited
UNITED STATES PATENTS

| | | | |
|---|---|---|---|
| 361,248 | 4/1887 | Winton | 206/818 X |
| 2,165,539 | 7/1939 | Dahlgren | 206/460 |
| 2,540,340 | 2/1951 | Linblade | 206/818 X |
| 3,361,252 | 1/1968 | Wise | 206/460 X |
| 3,389,784 | 6/1968 | Hendricks et al. | 206/460 X |
| 3,483,494 | 12/1969 | Cromie | 206/818 X |
| 3,586,160 | 6/1971 | Heimann | 206/447 |
| 3,723,061 | 3/1973 | Stahl | 206/370 X |

FOREIGN PATENTS OR APPLICATIONS

| | | | |
|---|---|---|---|
| 838,659 | 6/1960 | United Kingdom | 206/80 R |
| 926,698 | 4/1955 | Germany | 206/80 R |
| 294,298 | 7/1928 | United Kingdom | 206/818 |

*Primary Examiner*—William I. Price
*Assistant Examiner*—Steven E. Lipman
*Attorney, Agent, or Firm*—Lyon & Lyon

[57] ABSTRACT

A receiver for disposable surgical implements, principally surgical needles, including a pair of foldably connected pads, each having a penetrable top lamination and a penetration resisting bottom lamination. The top lamination of one embodiment is provided with a coating which is essentially non-adhesive when exposed to receive surgical implements to permit placement and penetration therein of the top lamination only as well as subsequent removal; but which is coadhesive with the coating on the other pad, when the two pads are folded into mutual pressure contact, thereby to secure surgical implements between the pads for disposal. In another embodiment, an adhesive coating is applied on one pad and is initially covered while the other pad is used to receive and removably retain surgical implements; the cover being removed and the adhesive coated pad pressed over the other pad and the surgical implements thereon to permit disposal. A further embodiment utilizes magnetic elements on the adhesive free pad for removable magnetic retention of the surgical implements prior to folding the pads for disposal.

4 Claims, 12 Drawing Figures

INVENTOR.
JOHN D. ELDRIDGE, JR.
BY
Lyon & Lyon
ATTORNEYS

INVENTOR.
JOHN D. ELDRIDGE, JR.
BY
ATTORNEYS

RECEIVER FOR DISPOSABLE SURGICAL IMPLEMENTS

This application is a continuation-in-part of my previous application, Ser. No. 868,317, filed Oct. 22, 1969, entitled RECEIVER FOR DISPOSABLE SURGICAL IMPLEMENTS and now abandoned; and is a continuation-in-part of my previous copending application, Ser. No. 182,588 filed Sept. 22, 1971, also entitled RECEIVER FOR DISPOSABLE SURGICAL IMPLEMENTS and also abandoned.

BACKGROUND OF THE INVENTION

The use of disposable surgical implements such as hypodermic needles, surgical needles and small surgical knives is increasing rapidly; however, this has resulted in an attendant increasing problem of injury and infection by accidental contact with the discarded implement. A typical practice is to use available containers, such as pill containers and other products. Such containers are not suitable for placement in reach of the surgeon, thus requiring a second handling and the attendant danger of injury. Adhesive pads have been used for packaging articles as exemplified in U.S. Pat. No. 3,389,784, a display of articles as exemplified in British Pat. No. 838,659 in which the adhesive pad is provided with a cover pad which is perforated or cut to form openings so that the articles may be pressed therein for removable contact with the underlying adhesive pad.

Such packages are incapable of meeting the requirements of surgical procedures. For surgery, the implement receiver must be stored in a sterile envelope until used, removed from the envelope and placed so as to be readily accessible to the doctor or nurse for placement of surgical implements therein; however the surgical implements should be removable for further use during the surgery. The surgical implements are handled by the surgeon or nurse who is wearing gloves. Any contact with a surface that would function as an adhesive could not be tolerated. Placing and retrieving of the surgical implement usually is done with two hands; thus, the need to hold the pad with one hand while removing the implement requires an adhesive free area. When surgery is completed, the surgical implements should be readily visible to facilitate accounting for all implements. Finally, the receiver should be capable of providing an essentially permanent protective enclosure for the surgical implements which will virtually eliminate any danger of contact with the surgical implements and consequent injury or infection.

SUMMARY OF THE INVENTION

The present invention is directed to a receiver for surgical implements which may be stored in a sterile envelope prior to use; then placed in a readily accessible location, and is summarized in the following objects:

First, to provide a receiver which is particularly intended for small sharp surgical implements, such as surgical needles, the receiver providing a sterile surface during surgery permitting removal if needed and also serves as collector for the surgical implements to facilitate accounting for all the implements; and which, after surgery, may be folded to enclose the surgical implements in such a manner as to avoid subsequent contact therewith and attendant risk of injury or infection.

Second, to provide a receiver, as indicated in the preceeding object, wherein the receiver includes a pair of pads, each having a top lamination formed of yieldable material capable of being penetrated by a sharp implement to retain the implement, and a penetration resisting bottom lamination, the pads being foldable to encase the surgical implements between their bottom laminations.

Third, to provide a receiver, as indicated in the preceeding objects, an embodiment of which utilizes a coating on the top surfaces of both pads which is essentially non-adhesive when exposed to receive the surgical implements but which is co-adhesive with the coating of the other pad, when the two pads are folded.

Fourth, to provide a receiver for surgical implements utilizing a pair of mutually foldable pads, one of which is free of adhesive, whereas the other pad is provided with an adhesive coating, initially provided with a non-adhesive cover, the adhesive free pad forming a surgical implement receiving surface.

Fifth, to provide a receiver as indicated in the preceeding object wherein the adhesive free pad is provided with magnet elements for removable magnetic retension of surgical implements thereon.

DESCRIPTION OF THE PREFERRED EMBODIMENT

Figure 1:
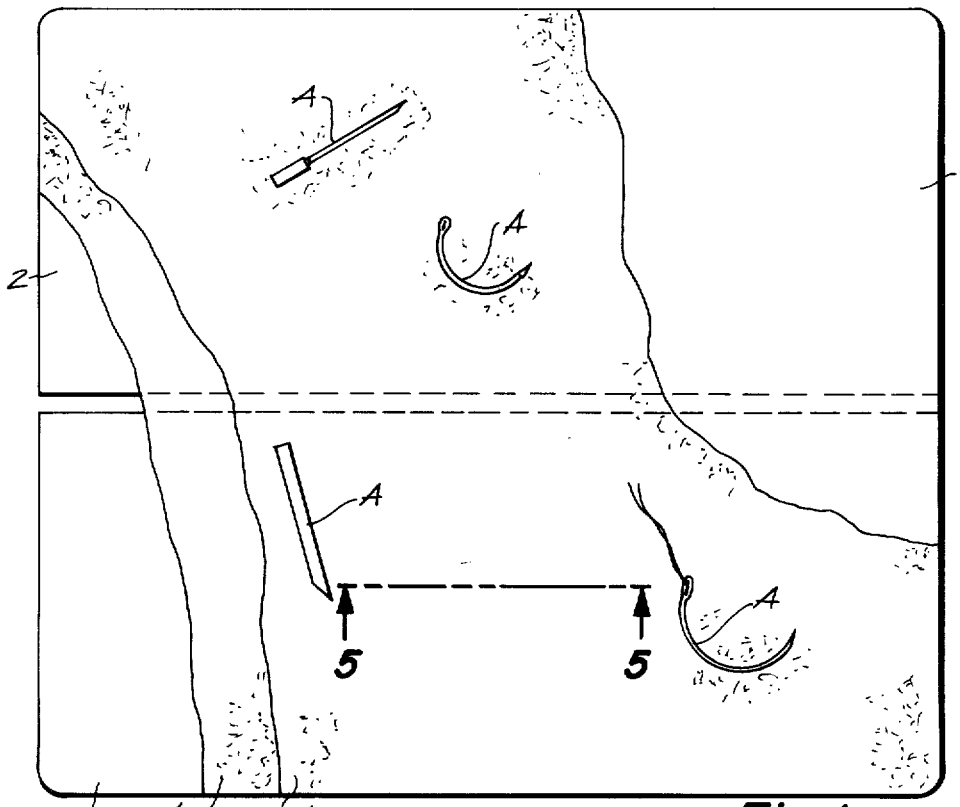
FIG. 1 is a plan view showing one form of the receiver for disposable surgical implements, the receiver being shown in its open position.
Figure 2:
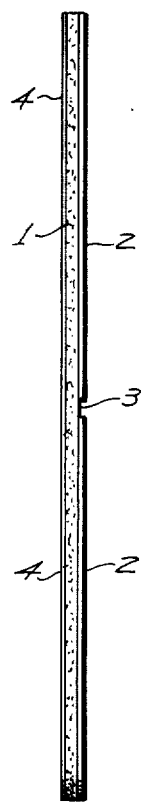
FIG. 2 is an edge view of the receiver in its open condition.
Figure 3:
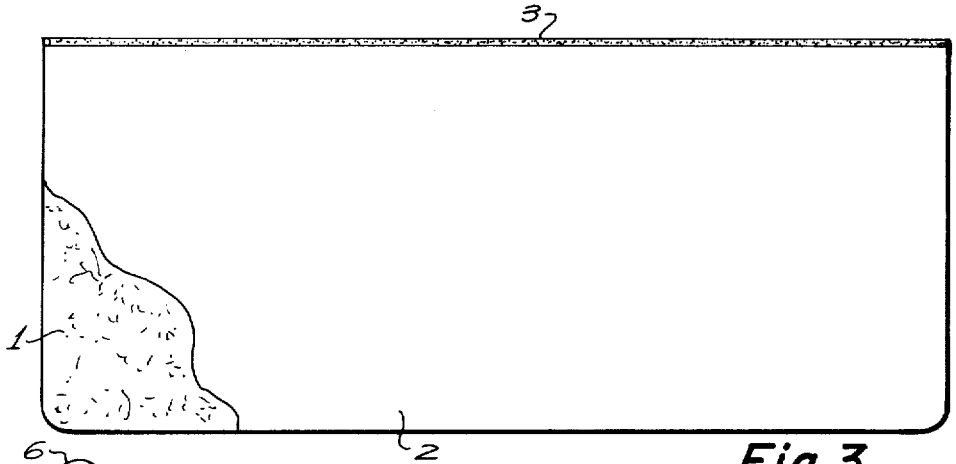
FIG. 3 is a plan view of the receiver shown in its folded condition.
Figure 4:
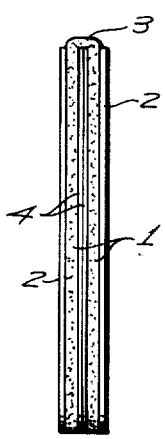
FIG. 4 is an edge view of the receiver shown in its folded condition.
Figure 5:
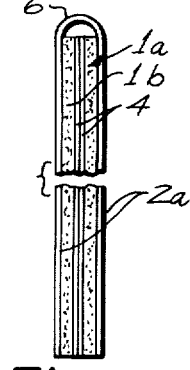
FIG. 5 is an enlarged fragmentary sectional view thereof, taken through 5—5 of FIG. 1.

Reference is first now directed to the construction shown in FIGS. 1 through 5. This construction utilizes a pad 1 formed of yieldable foamed plastic material for example, yieldable composition of a polyurethene or polystyrene capable of being penetrated by a sharp implement such as a surgical needle. The pad is provided with a pair of backing sheets 2, which are separated a short distance so that the pad 1 may form a hinge portion 3. The backing sheets are relatively resistant to penetration.

The pad is coated with a pressure sensitive adhesive 4, which is, per se conventional. Pressure sensitive adhesives are available which, when folded upon themselves, form a strong bond; however when exposed and not bonded to themselves, exhibit rather low if any, adhesiveness. If the pad is packaged in a folded condition, the pad is provided initially with a cover sheet 5, which is removed prior to use of the receiver. However the pad or several pads may be packaged in a sterile envelope or other container. In the latter case the back of one pad covers the coated surface of the succeeding pad.

The receiver illustrated in FIGS. 1 through 5 is used as follows:

The construction here illustrated is intended for use either outside of surgery; for example, in an examination room, or in surgery. The receiver is placed in convenient relation to the doctor or his nurse, first, however, removing the protective cover sheet 5. The small surgical implements A, principally surgical needles are discarded by placement on the pad. Slight adhesiveness may be permitted to retain the various implements, providing it is insufficient to stick to a surgical glove and upset the receiver. Alternatively, the point of the implement may be inserted laterally into the pad while in essentially flat relation to the pad so that it remains in a flat position.

At the appropriate time for implement count, which is considered good surgical practice, the implements are accounted for by counting the number on each receiver, if more than one is used. The pads of each receiver are then folded bringing the adhesive into mutual contact with the result that the adhesive bonds to itself and around the implements so that the implements are completely embedded and isolated by the backing sheets 2. As the two pads are pressed together, the area of mutual contact of the adhesive increases securing the pads together.

The pads may be formed of rigid foamed plastic, such as a more rigid composition of polystyrene. In this case, the plastic should be crushable to permit the implement to be embedded therein when folded; however the material should be resistant to chipping or breaking. For example, if a surgical needle is inserted, the particle may be carried by the needle or flip from the receiver into the operating zone.

Figure 6:
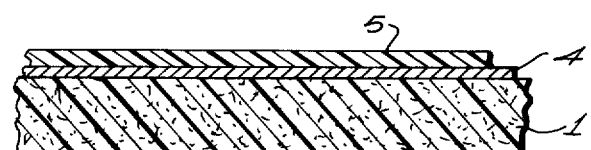
FIG. 6 is an edge view of a modified embodiment of the invention shown in its folded position.
Figure 7:
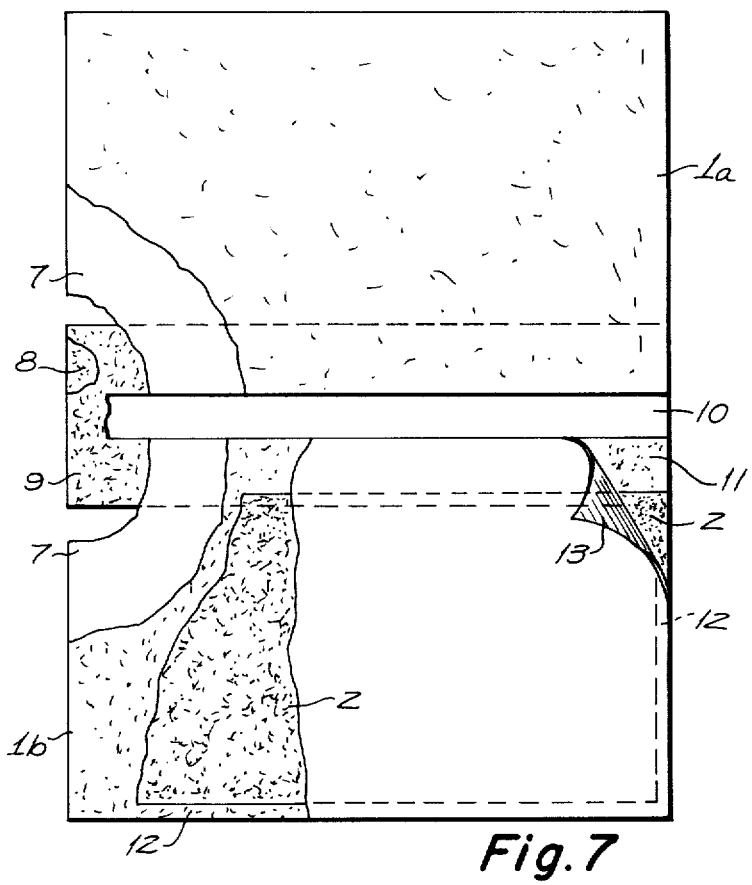
FIG. 7 is a plan view corresponding to FIG. 1, showing another embodiment of the invention.

Reference is directed to FIG. 6. Two pads 1a and 1b are utilized which, when coplanar, are separated a short distance from each other, and a single flexible, but penetration resistant, backing sheet 2a covers both pads and forms a connecting hinge element 6. Also a single continuous pad may be used which is compressible in the region of the hinge element 6, when the pad 2a is folded.

Reference is now directed to FIGS. 7 through 10. In this construction, as in FIG. 6, two pads 1a and 1b, which may be formed by either yieldable or crushable material are used, such as polyurethene or polystyrene foam. Each pad is provided with a relatively rigid penetration resistant backing sheet 7. The backing sheets are joined by a hinge strip 8 coated with a pressure sensitive adhesive 9. In order for the hinge to function, the pads are separated and the space therebetween is covered by a non-adhesive strip 10.

As illustrated, one pad is coated with a pressure sensitive adhesive 2; however, in this case a major uncoated margin 11 is formed adjacent the hinged edge of the pad and if desired, a minor uncoated margin 12 is formed along the remaining edges of the pad. A strippable cover sheet 13 covers the pad. The sheet 13 is coextensive with the pad so that particularly the margin of the sheet overlying the margin 11 may be readily grasped by a gloved hand to remove the sheet without contact with the adhesive.

In using this embodiment, the pad 1b initially remains covered and the surgical implements are placed on pad 1a, or inserted into the pad for retension. When use of the receiver is completed, the cover sheet 13 is stripped from pad 1b and pad 1b is folded over pad 1a and pressed to cause bonding engagement. It is, of course, essential that the adhesive bond readily to the uncoated surface when the pads are folded together.

Figure 8:
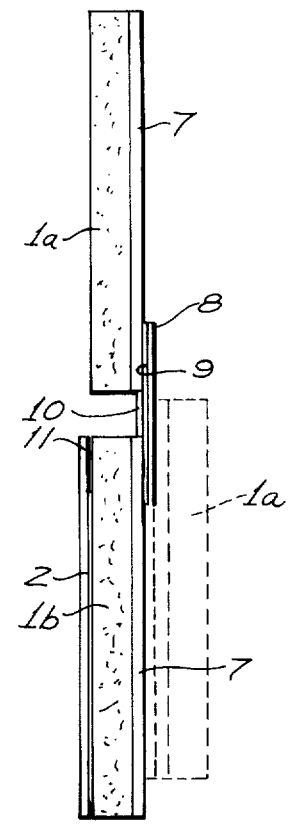
FIG. 8 is an edge view thereof, in its open condition with the thickness of the parts exaggerated for clarity and indicating by broken line a reverse folded portion.
Figure 9:
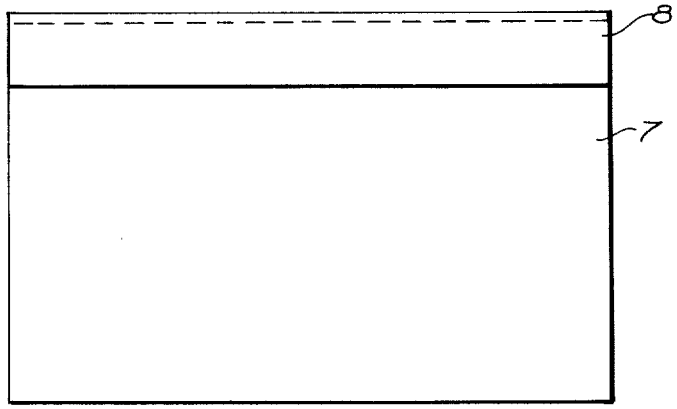
FIG. 9 is a plan view thereof in its folded condition.
Figure 10:
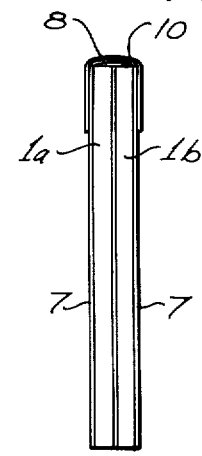
FIG. 10 is an edge view thereof in its folded condition.

It is possible to fold the uncoated pad 1a in front of the pad 1b as shown by dotted lines in FIG. 8 so that the uncoated pad only is exposed, thus minimizing the chance that an implement may be placed on the wrong pad.

Figure 11:
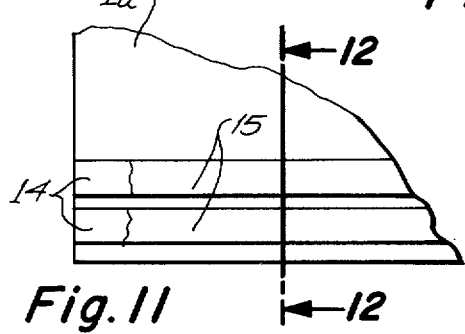
FIG. 11 is a fragmentary plan view showing a modified embodiment of the receiver.
Figure 12:
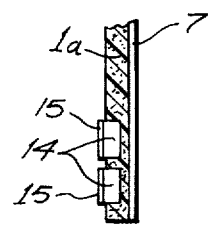
FIG. 12 is a fragmentary sectional view thereof taken through 12—12 of FIG. 11 with the thickness of the parts exaggerated.

Reference is now directed to FIGS. 11 and 12 in which one or several magnets 14 are pressed into the pad 1a which is free of adhesure coating. These may be formed of a plastic material in which magnetic particles are embedded as more fully set forth in my copending application Ser. No. 182,731 filed Sept. 27, 1971, now U.S. Pat. No. 3,727,658 issued Apr. 17, 1973. An impervious plastic laminate 15 may cover the magnets. The magnets are not positioned for mutual contact as in the previous patent, but are intended only to provide a low retention force, so that during surgery, surgical implements may be removed and replaced.

The magnet or magnets provide an alternative to inserting the points of the surgical implements into the pad material for retention. Also the magnets elevate the implements slightly and thus facilitate grasping the implements for removal. Still further, the magnets facilitate needle count. As each needle is discarded it is laid crosswise to the magnets with its pointed end directed inwardly and its threaded end at or projecting slightly beyond the pad. After the operation is completed, the needles are counted, then the sheet 13 is stripped from the pad 1b and the pad 1b is folded over the needles and bonded to the pad 1a.

If desired, the compressible pad may be omitted from one of the backing members, and this member provided with the adhesive coating. In this case the compressible pad may be increased in thickness so that when the backing member with its adhesive coating is pressed over the pad for bonding engagement therewith the surgical implements may be fully embedded therein.

Having fully described my invention it is to be understood that I am not to be limited to the details herein set forth, but that my invention is of the full scope of the appended claims.

I claim:

1. A receiver for pointed disposable surgical implements for holding such implements selectively accessible and for selectively encasing and holding said implements for disposal, comprising:
   a. a first and a second pad element formed of yieldable, penetrable foamed plastic material;
   b. a penetration resistant backing element for each pad element;
   c. hinge means foldably connecting the pad and backing elements to permit movement of the pad elements between an essentially coplanar position, and a mutually face-to-face contacting position;
   d. a pressure sensitive adhesive coating on the outer face of one of the pad elements, the outer face of the other pad element being adhesive free;

e. a removable protective lamination initially covering the adhesive coating, whereby said receiver may be arranged in said coplanar relation and implements placed on said adhesive free pad for selective removal and replacement and whereby said adhesive coated pad, with said protective lamination removed, may be folded over said other pad and implements thereon to adhere to said other pad and encase said implements between said pads and penetration resistant backing elements.

2. A receiver as defined in claim 1, wherein:

a. at least a selected margin of the cover sheet projects beyond the pad element area coated with adhesive to permit grasping of the cover sheet for removal without contact with the adhesive coating.

3. A receiver as defined in claim 1 wherein said backing elements are relatively rigid and spaced apart and wherein said hinge means comprise a flexible member spanning said space and having an adhesive coating adhering the same to said backing elements, and a nonadhesive covering for said adhesive coating between said backing elements.

4. A receiver as defined in claim 1, wherein:

a. magnet elements are embedded in said one pad for removably retaining magnetizable surgical implements thereon while the pad is exposed.

* * * * *